United States Patent [19]
Heckele et al.

[11] Patent Number: 5,712,518
[45] Date of Patent: Jan. 27, 1998

[54] ELECTRIC MOTOR DRIVE UNIT FOR SURGICAL TOOLS

[75] Inventors: Helmut Heckele; Jörg Kleih, both of Knittlingen, Germany

[73] Assignee: Richard Wolf GmbH, Knittlingen, Germany

[21] Appl. No.: 555,473

[22] Filed: Nov. 8, 1995

[30] Foreign Application Priority Data

Nov. 8, 1994 [DE] Germany .................. 44 39 799.2

[51] Int. Cl.$^6$ ................................................. H02K 7/14
[52] U.S. Cl. ................... 310/50; 310/47; 310/78; 310/75 R; 310/75 B; 51/181 R
[58] Field of Search ................. 310/47, 50, 75 R, 310/75 B, 78

[56] References Cited

U.S. PATENT DOCUMENTS

| | | | |
|---|---|---|---|
| 3,818,255 | 6/1974 | Wagner | 310/50 |
| 3,873,863 | 3/1975 | Pew | 310/50 |
| 4,164,670 | 8/1979 | Maher | 310/50 |
| 4,413,199 | 11/1983 | Fischer | 310/50 |
| 4,420,702 | 12/1983 | Mixner | 310/50 |
| 4,905,423 | 3/1990 | Van Laere | 51/181 R |
| 4,929,858 | 5/1990 | Konishi | 310/83 |
| 4,967,887 | 11/1990 | Annachino et al. | 192/21.5 |
| 5,013,950 | 5/1991 | Isozumi | 310/83 |
| 5,170,851 | 12/1992 | Kress et al. | 173/29 |
| 5,253,382 | 10/1993 | Beny | 15/22.1 |
| 5,298,821 | 3/1994 | Michel | 310/47 |

FOREIGN PATENT DOCUMENTS

| | | | |
|---|---|---|---|
| 2061724 | 10/1971 | Germany | 310/67 R |
| 3237197 | 4/1983 | Germany | 310/67 R |
| 3202193 | 8/1983 | Germany | 310/67 R |

*Primary Examiner*—Steven L. Stephan
*Assistant Examiner*—Elvin G. Enad
*Attorney, Agent, or Firm*—Cohen, Pontani, Lieberman & Pavane

[57] ABSTRACT

An electric motor drive unit for surgical tools, in which a drive consisting of a motor or motor gear unit is connected to, and electrically insulated from a clutch for the tool by a shaft, and in which the drive as well as current-carrying components are electrically insulated from a housing which accomodates said drive and current-carrying components. To achieve an electrical isolation of the current-carrying components from the tool and the gripping surface of the housing, the shaft, at least over part of its length, is made from an insulating material and runs through a seal which is supported in the housing and sealingly divides the housing into a first and second chamber, of which the first chamber accomodates the drive and the second chamber accomodates the clutch for the tool, said tool being inserted into a distal opening in the housing in the second chamber and connectable to the clutch.

10 Claims, 5 Drawing Sheets

5,712,518

ELECTRIC MOTOR DRIVE UNIT FOR SURGICAL TOOLS

BACKGROUND OF THE INVENTION

1. Field of the Invention

The present invention relates to an electric motor drive unit for surgical tools, in which the electrical drive unit is electrically insulated from the housing and other components of the drive unit.

2. Description of the Prior Art

German Patent document DE-A-3237197 discloses a magnetic clutch which transmits the rotation of the motor shaft or gear shaft of the motor gear unit to the tool without contact. Such a clutch however cannot transmit large mechanical forces to the tool. Furthermore, such drive units do not always provide a perfect electrical isolation of the electrical components and therefore sufficient protection against accidental contact cannot be guaranteed.

SUMMARY OF THE INVENTION

It is the object of the present invention to provide an electric motor drive which is securely electrically insulated and with which large motive forces can be transmitted to a surgical tool.

In accordance with the present invention, this object is achieved in that the shaft of the drive unit, at least over part of its length, is made from an electrically insulating material and runs through a seal which is supported in the housing and sealingly divides the housing into a first and second chamber. The first chamber accomodates the drive and the second chamber accomodates the clutch for the tool. The tool is being inserted into a distal opening in the housing in the second chamber and is connected to the clutch.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the drawings, wherein like reference numerals delineate similar elements throughout the several views.

DETAILED DESCRIPTION OF THE PRESENTLY PREFERRED EMBODIMENTS

Figure 1:
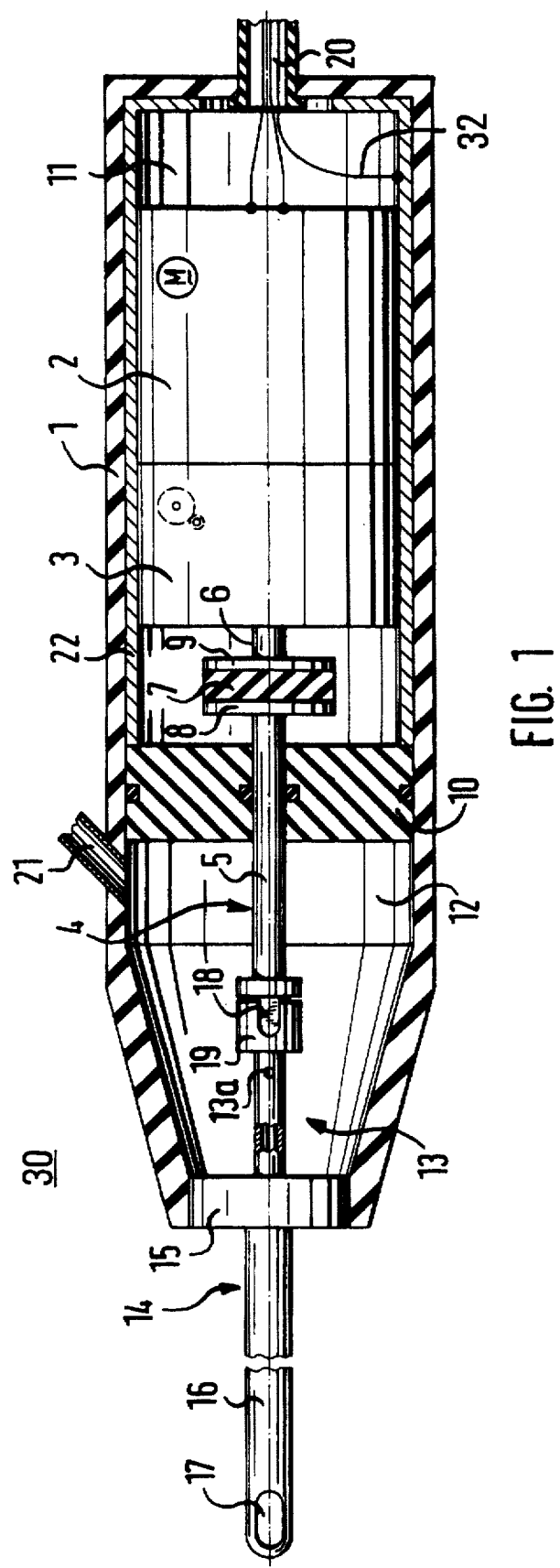
FIG. 1 is a longitudinal cross-sectional view of a first embodiment of an electric motor drive unit for surgical tools of the present invention.

A drive unit constructed in accordance with the present invention is labelled with the general number 30 and is especially useful as an electric motor drive unit for surgical tools.

The drive unit shown in FIGS. 1 to 5 comprises a housing 1, the perimeter of which may be grasped by the operator's hand. The drive unit 30 is enclosed by the housing 1 and comprises an electric motor 2 and a gear 3 with a shaft 4. The shaft 4 is comprised of first and second shaft parts 5 and 6 connected by a disc 7 made of electrically insulating material, and for this purpose is provided with first and second flanges 8 and 9 opposite each other and which are connected to the disc 7 for example with adhesive, or by interlocking or force fitting.

The shaft 4 is arranged with its first shaft part 5 passing through a seal 10 which acts as a bearing, the seal 10 dividing the housing 1 into a first chamber 11 accomodating the motor gear unit 2, 3, and a second chamber 12 into which the free end of the first shaft part 5 protrudes and is connected to the surgical tool 13 which forms part of the working unit 14. The working unit 14 comprises a collar 15 mounted at the distal end of the housing 1 and a shank 16 comprising a window 17 at its distal end. The window 17 of the surgical tool 13 is used to contact the tissue to be removed and such, that the tissue goes through the window 17 into the working area of the surgical tool 13 and can be removed through tube 21.

The surgical tool 13 is connected to the drive unit 30 via the first shaft part 5, which for this purpose is provided with a driving tenon 18 forming part of the clutch, the driving tenon 18 interlocking with a complementary shaped clutch part 19 of the surgical tool 13. The surgical tool 13 may be tube shaped and provided with an opening 13a.

The electrical power for the drive unit 30 is supplied by a source of electric power (not shown) through an electrical connecting cable 20 which is introduced into the first chamber 11 and connected to the motor gear unit 2, 3. The tube 21 of the second chamber 12 is used to introduce fluid for flushing, the fluid being able to flow through the annulus in the surgical tool 13 and the shank 16 or through the tube shaped tool itself, to the distal end of the shank 16 and through the window 17 of the shank 16 into the area of treatment, and can be aspirated back the same way with the tissue to be removed.

With the object of the present invention in mind, it is important that there is electrical isolation between the current-carrying parts of the tool 13 and the gripping surface of the housing 1. According to the embodiment of the invention of FIG. 1, this is achieved by making the disc 7 mounted to the shaft 4 from an electrically insulating material, and by also making the housing 1, and the seal 10 which is tightly fitted into it, from an electrically insulating material. The seal 10 may, for example, be made of a ceramic material. The seal 10 prevents flushing fluid in the second chamber 12 from entering the first chamber 11 which accomodates the motor gear unit 2, 3. Since the motor gear unit 2, 3 is electrically insulated from the outside by the housing 1, the operator cannot contact any current-carrying components. Moreover, the motor gear unit 2, 3 is surrounded by a metallic bush 22 which functions as a shielding against interference signals, thereby improving electromagnetic compatability.

Figure 2:
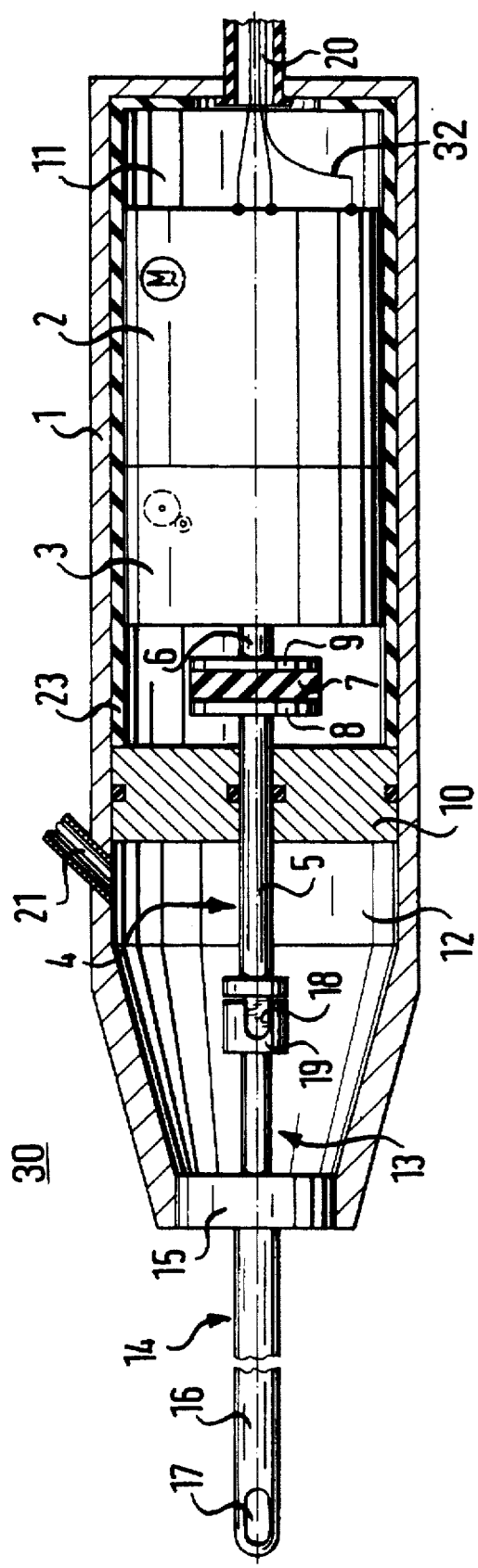
FIG. 2 is a longitudinal cross-sectional view of a second embodiment of an electric motor drive unit for surgical tools of the present invention.

The drive unit 30 according to FIG. 2 comprises a housing 1 made from metal. The motor gear unit 2, 3 is surrounded by a non-metallic bush 23 made from insulating material and inserted into the housing 1. In this embodiment, the seal 10 may be made of metal whereas the disc 7 is made of an electrically insulating material, as in the embodiment shown in FIG. 1.

Figure 3:
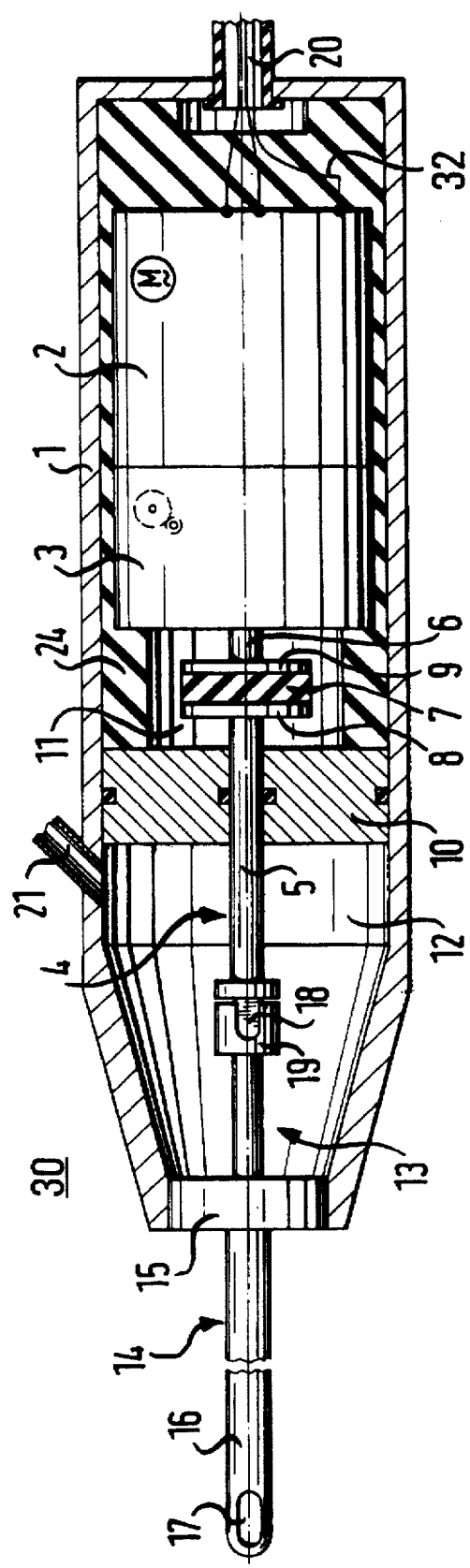
FIG. 3 is a longitudinal cross-sectional view of a third embodiment of an electric motor drive unit for surgical tools of the present invention.
Figure 4:
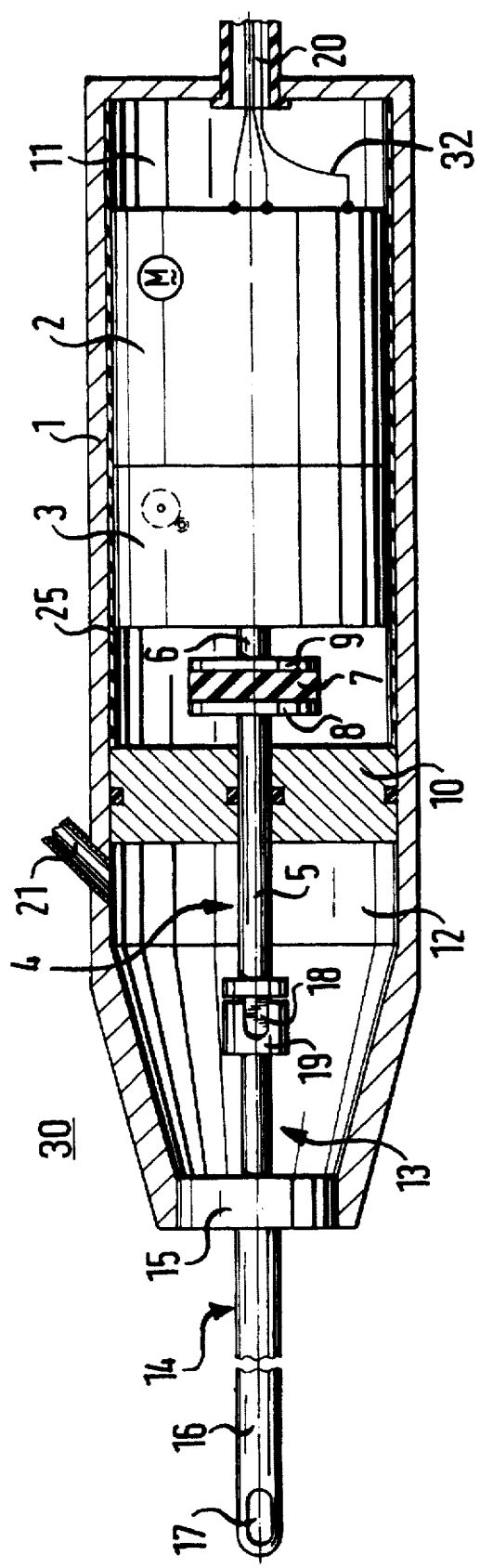
FIG. 4 is a longitudinal cross-sectional view of a fourth embodiment of an electric motor drive unit for surgical tools of the present invention.

With the drive unit 30 according to FIG. 3, the insulation of the motor gear unit 2, 3 from the metallic housing 1 is effected, as with the embodiment of FIG. 2, by a cover 24 made of an electrically insulating material into which the motor gear unit 2, 3 is housed. Referring next to FIG. 4, the insulation between the motor gear unit 2, 3 and the housing 1 is effected by an electrically insulating layer 25 with which the metallic housing 1 is lined, at least around the area of the first chamber 11.

Figure 5:
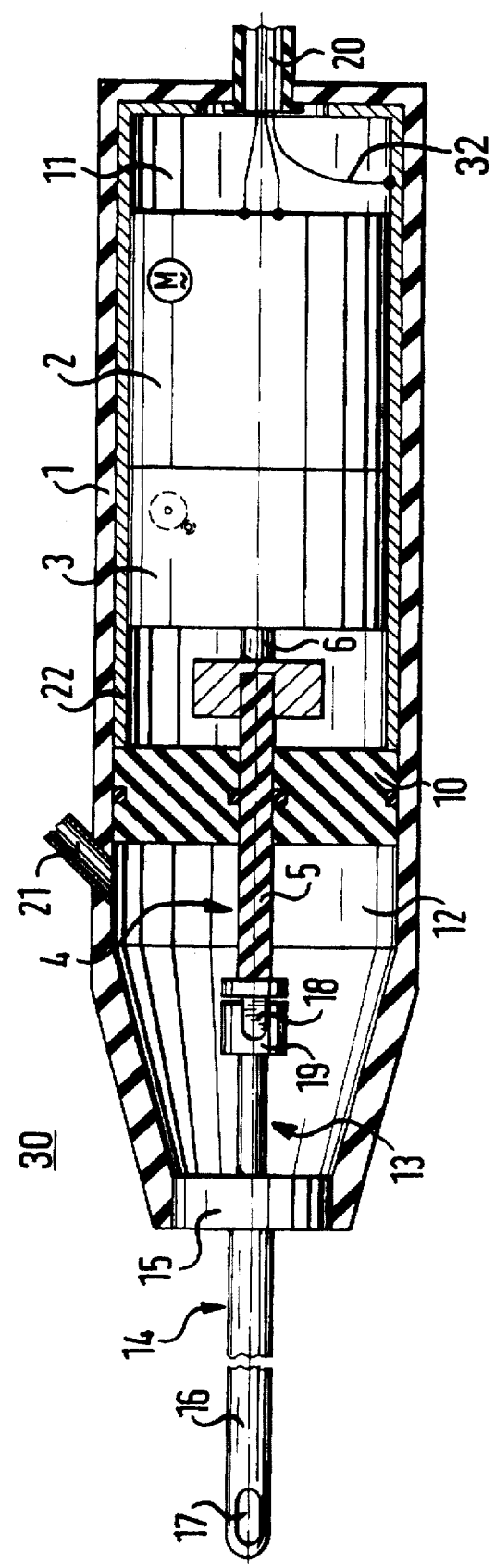
FIG. 5 is a longitudinal cross-sectional view of a fifth embodiment of an electric motor drive unit for surgical tools of the present invention.

Lastly, in the embodiment shown in FIG. 5, the electrical insulation of the current-carrying parts from the surgical tool 13 may be achieved by manufacturing the first shaft 4 over at least part of its length from electrically insulating material, in this case the shaft part 5. The drive unit is arranged as shown in FIG. 1, i.e., the housing 1 and seal 10 are made from electrically insulating material.

In each described embodiment of the drive unit 30, a protective contact 32 is either connected to the metallic bush 22 surrounding the motor gear unit 2, 3, as shown in FIGS. 1 and 5, or directly to the motor housing as shown in FIGS. 2, 3 and 4.

The gear 3 may be omitted should a gearing up or down of the r.p.m. not be required. The drive unit is also suitable for oscillatory driven tools should the drive and clutch be so designed and the shaft, as an operating rod for the tool, then arranged with a bearing in the housing for axial movement.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

We claim:

1. An electric motor drive unit for a surgical tool, comprising:
    a housing having an aperture at a distal end thereof;
    a seal sealingly mounted within said housing so as to divide said housing into a first, proximal and a second, distal chamber, said seal having an aperture passing therethrough so as to connect the first and second chambers of said housing;
    an electrical drive means mounted within the first chamber of said housing for providing mechanical power in response to an electrical input, said drive means being electrically insulated from said housing;
    a shaft having proximal and distal ends, the proximal end thereof being operatively connected to said drive means and being comprised of electrically insulating material, said shaft extending sealingly through the aperture of said seal;
    a clutch operatively connected to the distal end of said shaft, said clutch being located within said second chamber of said housing; and
    a surgical tool, a proximal end thereof extending through the aperture of said housing and being operatively connected to said clutch.

2. The electric motor drive unit of claim 1, further comprising a tenon means interposed between said shaft and said clutch for operatively connecting said shaft to said clutch.

3. The electric motor drive unit of claim 1, further comprising a bush interposed between said drive means and said housing, said bush being comprised of electrically conducting material, and wherein said housing and said seal are comprised of electrically insulating material.

4. The electric motor drive unit of claim 1, further comprising a bush interposed between said drive means and said housing, said bush being comprised of electrically insulating material, and wherein said housing is comprised of a metallic material.

5. The electric motor drive unit of claim 1, further comprising a cover comprised of an electrically insulating material, said cover positioned about said drive means so as to electrically isolate said drive means from said housing and said seal.

6. The electric motor drive unit of claim 5, wherein said housing and said seal are comprised of metallic material.

7. The electric motor drive unit of claim 1, further comprising a layer comprised of electrically insulating material, said layer being attached to an inner surface of said housing and interposed between said housing and said drive means.

8. The electric motor drive unit of claim 7, wherein said housing is comprised of metallic material.

9. The electric motor drive unit of claim 1, further comprising a disc formed in said shaft between the proximal and distal ends thereof, said disc being formed of an electrically insulating material.

10. The electric motor drive unit of claim 9, wherein at least one of the proximal and distal ends of said shaft are comprised of metallic material.

* * * * *